United States Patent [19]

Butler

[11] Patent Number: 4,638,006

[45] Date of Patent: Jan. 20, 1987

[54] AMNESIA REVERSAL WITH N,N-DIALKYLAMINOALKYL-HEXAHYDRO-5-OXO 1H-PYRROLIZINE-3-CARBOXAMIDES

[75] Inventor: Donald E. Butler, Holland, Mich.

[73] Assignee: Warner Lambert Company, Morris Plains, N.J.

[21] Appl. No.: 779,712

[22] Filed: Sep. 24, 1985

[51] Int. Cl.$^4$ .................. A61K 31/445; C07D 487/04
[52] U.S. Cl. .................................. 514/323; 514/413; 546/200; 548/453; 548/532; 548/533
[58] Field of Search ........................ 548/453; 546/200; 514/323, 413

[56] References Cited

U.S. PATENT DOCUMENTS 4,145,347  3/1979  L'Italien et al. .................... 546/208
4,563,469  1/1986  Butler et al. .................... 548/453 X

OTHER PUBLICATIONS

Davies, W. et al., Tetrahedron, 1962, 18 405–12.

Primary Examiner—Richard A. Schwartz
Attorney, Agent, or Firm—Elizabeth M. Anderson

[57] ABSTRACT

A unique series of N,N-dialkylaminoalkyl-hexahydro-5-oxo-1H-pyrrolizine-3-carboxamides are disclosed. These compounds are useful as agents for the reversal of amnesia. Intermediates for preparing the compounds, pharmaceutical compositions containing them, and methods for using the pharmaceutical compositions for treating senility and for the reversal of amnesia are described.

22 Claims, No Drawings

AMNESIA REVERSAL WITH N,N-DIALKYLAMINOALKYL-HEXAHYDRO-5-OXO 1H-PYRROLIZINE-3-CARBOXAMIDES

BACKGROUND OF THE INVENTION

The compounds of the instant invention are a unique series of N,N-dialkylaminoalkyl-hexahydro-5-oxo-1H-pyrrolizine-3-carboxamides which are useful for the treatment of senility and the reversal of amnesia.

5-Carboethoxy-2-pyrrolecarboxaldehyde is described in Tetrahedron, 1962, 18, 405–12. This same article also mentions 5-carboethoxypyrrole-2-propanoic acid ethyl ester. In the present invention the 5-carboethoxypyrrole-2-propanoic acid benzyl ester was made to allow differentiation between the two acids in the one molecule.

SUMMARY OF THE INVENTION

One aspect of the present invention is a compound of the formula

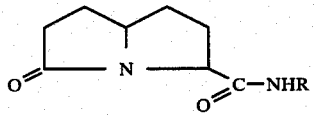
V wherein R is $CH_2CH_2NR'R''$, $CH_2CH_2CH_2NR'R''$, $CH_2CH_2CH_2CH_2NR'R''$, and R' and R'' are each independently a straight or branched alkyl of from one to six carbon atoms; or when attached to the nitrogen they form a cis or trans 2,6-dimethylpiperidine which may optionally be substituted with one or more alkyl groups of from one to four carbon atoms, or a pharmaceutically acceptable acid addition salt thereof.

Another aspect of the present invention is a method of preparing a compound of Formula V which comprises:
(a) treating a 5-carboalkoxy-2-pyrrolecarboxaldehyde with a carboxyphenylmethylmethylenetriaryl phosphorane to form
(b) a mixture of cis- and trans-5-carboalkoxy-2-pyrrolalkenoic acid phenylmethyl esters which are catalytically hydrogenated to form
(c) the corresponding 5-carboalkoxy-2-pyrrole alkanoic acid which is further hydrogenated to give
(d) 5-carboethoxy-2-pyrrolidinepropanoic acid which is dehydrated to give
(e) the hexahydro-5-oxo-1H-pyrrolizine-3-carboxylic acid ethyl ester which
(f) is treated with a N,N-dialkylaminoalkyl amine to form
(g) corresponding N,N'-dialkylaminoalkyl hexahydro-5-oxo-1H-pyrrolizine-3-carboxamides.

A third aspect of the present invention is a pharmaceutical composition which comprises an effective amount of a compound of structural Formula V above in combination with a pharmaceutically acceptable carrier.

A fourth aspect of the present invention is a method of treating senility in a mammal comprising administering to a mammal the above identified composition in unit dosage form effective for treating senility.

A fifth aspect of the present invention is a method of reversing amnesia in a mammal comprising administering to the mammal the above identified pharmaceutical composition in unit dosage form for reversing amnesia.

DETAILED DESCRIPTION OF THE INVENTION

Compounds of the formula:

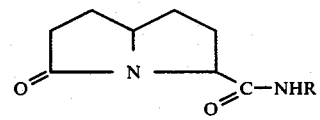
V wherein R is as defined above, comprise the present invention.

The compounds include solvates and hydrates and pharmaceutically acceptable salts of the basic compounds of the above formula.

The term pharmaceutically acceptable acid addition salt is intended to mean a relatively nontoxic acid addition salt, either from inorganic or organic acids, such as, for example, hydrochloric, sulfuric, phosphoric, acetic, citric, oxalic, malonic, salicyclic, malic, gluconic, fumaric, succinic, ascorbic, maleic, methanesulfonic, and the like. The salts are prepared by contacting the free base form with a sufficient amount of the desired acid to produce a salt in a conventional manner. The free base forms may be regenerated by treating the salt form with a base.

The alkyl groups of the present invention comprise both straight and branched carbon chains of from one to about six carbon atoms. Representatives of such groups are methyl, ethyl, isopropyl, 3-methyl, pentyl, and the like.

In addition, stereoisomerism is possible in the compounds of the present invention. Also, since the two rings are not completely flat, isomerism is possible in that the carboxamide may be on the exo- or endo-side of the molecule.

The present invention contemplates all geometric isomers, and stereoisomers of the compounds depicted generically by structural Formula V given above.

The terms "stereoisomers," "stereoisomerism," "optical isomerism," "optical isomers," "geometrical isomerism," and "geometrical isomers" as used throughout this specification and appended claims are those commonly employed by practitioners of the organic chemical art, specifically as defined on pages 1–6 of Eliel, "Stereochemistry of Carbon Compounds," McGraw-Hill, New York, 1962, incorporated herein by reference.

The preferred compounds are those of Formula V when R is $CH_2CH_2NR'R''$, $CH_2CH_2CH_2NR'R''$, or $CH_2CH_2CH_2CH_2NR'R''$, wherein R' and R' are each independently $CH_3$, $C_2H_5$, $CH(CH_3)_2$, or when taken together with the nitrogen to which they are joined form a cis- or trans-isomer of 2,6-dimethyl piperidine.

Particularly valuable compounds falling within the scope of the present invention include the following compounds and their stereoisomers:
N-[2-[N,N-bis(1-methylethyl)amino]ethyl]-hexahydro-5-oxo-1H-pyrrolizine-3-carboxamide;
N-[2-[2,6-dimethyl-1-piperidinyl]ethyl]hexahydro-5-oxo-1H-pyrrolizine-3-carboxamide, cis- and transisomers;
N-[N,N-dimethylaminoethyl]-hexahydro-5-oxo-1H-pyrrolizine-3-carboxamide;

N-[N,N-diethylaminoethyl]-hexahydro-5-oxo-1H-pyrrolizine-3-carboxamide;

N-[3-N,N-[bis(1-methylethyl)amino]propyl]-hexahydro-5-1H-pyrrolizine-3-carboxamide;

N-[3-[2,6-dimethyl-1-piperidinyl]propyl]-hexahydro-5-oxo-1H-pyrrolizine-3-carboxamide, cis- and trans-isomers;

N-[3-[N,N-dimethylamino]propyl]-hexahydro-5-oxo-1Hpyrrolizine-3-carboxamide;

N-[3-[N,N-diethylamino]propyl]-hexahydro-5-oxo-1H-pyrrolizine-3-carboxamide.

The above compounds may be prepared by treating a hexahydro-5-oxo-1H-pyrrolizine-3-carboxylic acid alkyl ester with a N,N-dialkylaminoalkyl amine to form the corresponding N,N-dialkylaminoalkyl carboxamide and, if desired, converting the free base to a pharmaceutically acceptable acid salt thereof.

The reaction is carried out in two steps. First the reactants are heated to 20°–30° C. for 12 to 36 hours, and then the reaction mixture is heated to 70°–90° C. for an additional 12–36 hours. The solution is concentrated at reduced pressure and then distilled.

The preferred reaction conditions are heating at 25° C. for 24 hours followed by heating at 80° C. for an additional 24 hours. The vacuum distillation is done at 0.025 torr.

Alternatively, the above compounds may be prepared by treating a hexahydro-5-oxo-1H-pyrrolizine-3-carboxylic acid with a phosphorylazide and then treating the reaction product with an N,N-dialkylaminoalkyl amine to form the corresponding carboxamide and, if desired, converting the free base to a pharmaceutically acceptable acid salt thereof. The alternate reaction is carried out by dissolving the above ester in a solvent such as dichloromethane, tetrachloroethane, or dimethylformamide. A phosphoryl azide is added and the reaction is carried of at from −10° to 10° C. for 1.5 to 2.5 hours. Subsequently a solution of an N,N-dialkylaminoalkyl amine is added dropwise and the mixture is stirred for 12 to 36 hours and then purified.

In the preferred reaction conditions the solvent is dichloromethane. The preferred azide is diphenyl phosphorylazide. Preferably the reaction is carried out at 0° C. for two hours. The N,N-dialkylaminoalkyl amine is a solution of N,N-di-(2-methylethyl)aminoethylamine which is added dropwise and then stirred for 24 hours.

The starting material, a hexahydro-5-oxo-1H-pyrrolizine-3-carboxylic acid alkyl ester, is prepared by the following schematic procedure.

SCHEMATIC

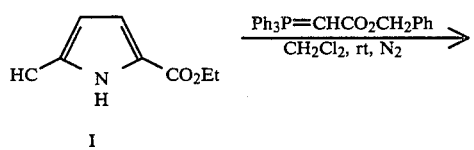

-continued
SCHEMATIC

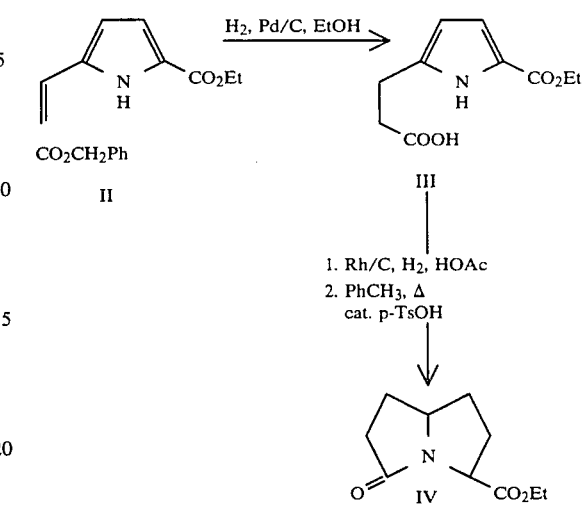

The compounds of the present invention are useful for treating senility or for reversing amnesia.

The effectiveness of the aforementioned compounds is determined by a test designed to show a compound's ability to reverse amnesia produced by electroconvulsive shock. The test is fully described in U.S. Pat. No. 4,145,347, issued Mar. 20, 1979, and is herein incorporated by reference. The only differences being that the test compounds in the present instance are administered orally and the length of the electroconvulsive shock is 1.0 seconds in duration.

The following criteria are used in interpreting the percent of amnesia reversal scores: 40% or more (active=A), 25–39% (borderline=C), and 0–24% (inactive=N).

Thus, a representative example of amnesia reversal is the compound wherein R is $CH_2CH_2N[CH(CH_3)_2]_2$ administered orally at a dose of 100 mg/kg showed 60% activity, at 40 mg/kg showed 40%, and "even" at 1 mg/kg showed 30% amnesia reversal.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogenously therein by stirring. The molten homogeneous mixture is then poured into convenient sized molds, allowed to cool, and thereby solidify.

Liquid form preparations include solutions, suspensions, and emulsions. As an example may be mentioned water or water propylene glycol solutions for parenteral injection. Liquid preparations can also be formulated in solution in aqueous polyethyleneglycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such as used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

Preparation of
N-[2-[N,N-bis(1-methylethyl)amino]ethyl]-hexa-hydro-5-oxo-1H-pyrrolizine-3-carboxamide A solution of hexahydro-5-oxo-1H-pyrrolizine-3-carboxylic acid ethyl ester (5.0 g, 0.0254 mol) in N,N-di-(2-methylethyl)aminoethylamine (10 g, 0.0693 mol) is stirred at room temperature 24 hours and heated at 80° C. for 24 hours. The solution is concentrated at reduced pressure and distilled to yield N-[2-[N,N-bis(1-methylethyl)amino]ethyl]-hexahydro-5-oxo-1H-pyrrolizine3-carboxamide, bp 155°–165° C. at 0.025 Torr.

EXAMPLE 2

Preparation of
N-[2-[2,6-dimethyl-1-piperidinyl]ethyl]hexahydro-5-oxo-1H-pyrrolizine-3-carboxamide, transisomer A solution of hexahydro 5-oxo-1H-pyrrolizine-3-carboxylic acid ethyl ester (5.0 g, 0.0254 mol) in trans-2,6-dimethylpiperidinoethylamine (15.6 g, 0.1 mol) is stirred at room temperature 24 hours and heated at 80° C. for 24 hours. The solution is concentrated at reduced pressure and distilled to yield N-[2-[2,6-dimethyl-1-piperidinyl]ethyl]-hexahydro-5-oxo-1H-pyrrolizine-3-carboxamide, trans-isomer.

EXAMPLE 3

Preparation of
N-[N,N-dimethylaminoethyl]-hexahydro-5-oxo-1H-pyrrolizine 3-carboxamide A solution of hexahydro-5-oxo-1H-pyrrolizine-3-carboxylic acid ethyl ester (5.0 g, 0.0254 mol) in N,N-dimethylaminoethylamine (9.8 g, 0.11 mol) is stirred at room temperature 24 hours and heated at 80° C. for 24 hours. The solution is concentrated at reduced pressure and distilled to yield N-[N,N-dimethylaminoethyl]-hexahydro-5-oxo-1H-pyrrolizine-3-carboxamide.

EXAMPLE 4

Preparation of
N-[N,N-diethylaminoethyl]-hexahydro-5-oxo-1H-pyrrolizine-3-carboxamide A solution of hexahydro-5-oxo-1H-pyrrolizine-3-carboxylic acid ethyl ester (5.0 g, 0.0254 mol) in N,N-diethylaminoethylamine (23.2 g, 0.2 mol) is stirred at room temperature 24 hours and heated at 80° C. for 24 hours. The solution is concentrated at reduced pressure and distilled to yield N-[N,N-diethylamino-ethyl]hexahydro-5-oxo-1H-pyrrolizine-3-carboxamide

EXAMPLE 5

Preparation of N-[3-[2,6-dimethyl 1-piperidinyl]propyl]hexahydro-5-oxo-1H-pyrrolizine-3-carboxamide cis-isomer A solution of hexahydro-5-oxo-1H-pyrrolizine-3 carboxylic acid ethyl ester (5.0 g, 0.0254 mol) in cis-3-[2,6-dimethylpiperidinyl]propylamine (34 g, 0.2 mol) is stirred at room temperature 24 hours and heated at 80° C. for 24 hours. The solution is concentrated at reduced pressure and distilled to yield N-[3-[2,6-dimethyl-1-piperidinyl]propyl]hexahydro-5 oxo1H-pyrrolizine-3-carboxamide.

EXAMPLE 6

Preparation of N-[3-[2,6-dimethyl-1-piperidinyl]propyl]hexahydro-5-oxo-1H-pyrrolizine-3-carboxamide, transisomer A solution of hexahydro-5-oxo-1H-pyrrolizine-3-carboxylic acid ethyl ester (5.0 g, 0.0254 mol) in trans-3-[2,6-dimethylpiperidinyl]propylamine (34 g, 0.2 mol) is stirred at room temperature 24 hours. The solution is concentrated at reduced pressure and distilled to yield N-[3-[2,6-dimethyl-1-piperidinyl]propyl]-hexahydro-5-oxo-1H-pyrrolizine-3-carboxamide, trans-isomer.

EXAMPLE 7

Preparation of N-[3-[N,N-dimethylamino]propyl]hexahydro-5-oxo-1H-pyrrolizine-3-carboxamide A solution of hexahydro-5-oxo-1H-pyrrolizine-3-carboxylic acid ethyl ester (5.0 g, 0.0254 mol) in 3-N,N-dimethylaminopropylamine (20.4 g, 0.2 mol) is stirred at room temperature 24 hours and heated at 80° C. for 24 hours. The solution is concentrated at reduced pressure and distilled to yield N-[3-[N,N-dimethyl-amino]-propyl]-hexahydro-5-oxo-1H-pyrrolizine-3-carboxamide.

EXAMPLE 8

Preparation of N-[3-[N,N-diethylamino]propyl]-hexahydro-5-oxo-1H-pyrrolizine-3-carboxamide A solution of hexahydro-5-oxo-1H-pyrrolizine-3-carboxylic acid ethyl ester (5.0 g, 0.0254 mol) in 3-N,N-diethylaminopropyl amine (13 g, 0.1 mol) is stirred at room temperature 24 hours and heated at 80° C. for 24 hours. The solution is concentrated at reduced pressure and distilled to yield N-[3-[N,N-diethylamino]propyl]-hexahydro-5-oxo-1H-pyrrolizine-3-carboxamide.

EXAMPLE 9

Alternate Preparation of N-[2-[N,N-bis(1-methylethyl)amino]ethyl]-hexahydro-5-oxo-1H-pyrrolizine-3-carboxamide.

A solution of hexahydro-5-oxo-1H-pyrrolizine-3-carboxylic acid (16.9 g, 0.1 mol) in dichloromethane (500 ml) at 0° C. is treated with diphenylphosphorylazide (0.1 mol) and stirred two hours. A solution of N,N-di-(2-methylethyl)aminoethylamine (14.4 g, 0.1 mol) is added dropwise and the mixture is stirred 24 hours. The solution is filtered and concentrated at reduced pressure. The product is purified by chromatography on $SiO_2$ (elution with $CH_2Cl_2:CH_3OH$; 90:10 saturated with anhydrous $NH_3$ to give N-[2-[N,N-bis(1-methylethyl)amino]ethyl]-hexahydro-5-oxo-1H-pyrrolizine-3-carboxamide.

Synthesis of Requisite Intermediates

EXAMPLE A

Preparation of hexahydro-5-oxo-1H-pyrrolizine-3-carboxylic acid ethyl ester

A solution of 5-carboethoxy-2-pyrrolidinepropanoic acid (21.1 g, 0.098 mol) in toluene (250 ml) is refluxed 18 hours removing water using a Dean-Stark trap.

The solution is concentrated at reduced pressure and distilled to yield hexahydro-5-oxo 1H-pyrrolizine-3-carboxylic acid ethyl ester, bp 105°–110° C. at 0.2 Torr.

EXAMPLE B

Preparation of 5-carboethoxy-2-pyrrolidinepropanoic acid

A solution of 5-carboethoxy-2-pyrrolepropanoic acid (114 g, 0.54 mol) in glacial acetic acid (1100 ml is treated with hydrogen gas in the presence of 10% Rh/C (5 g). After hydrogen uptake is complete, the suspension is filtered.

The filtrate is concentrated at reduced pressure to yield crude 5-carboethoxy 2-pyrrolidinepropanoic acid, which is used as is.

EXAMPLE C

Preparation of 5-carboethoxy-2-pyrrolepropanoic acid

A solution of 5-carboethoxy-2-pyrrolepropenoic acid phenylmethyl ester (16.5 g, 0.722 mol) in ethanol (2 l) is treated with hydrogen gas in the presence of 20% Pd/C (2 g). After the hydrogen uptake is complete, the suspension is filtered and concentrated at reduced pressure to yield a white solid. The solid is washed with anhydrous diethyl ether and dried in vacuo to yield 5-carboethoxy-2-pyrrolepropanoic acid, mp 126°–128° C.

EXAMPLE D

Preparation of 5-carboethoxy-2-pyrrolepropenoic acid phenylmethyl ester cis- and trans-isomers A solution of 5-carboethoxy-2-pyrrolecarboxaldehyde (105.5 g, 0.631 mol) in dichloromethane (1 l) is added dropwise with stirring to a solution of carboxyphenylmethylmethylenetriphenylphosphorane (260 g) in dichloromethane (1 l). The solution is stirred at room temperature 24 hours. The solution is concentrated and the oily solid is washed with anhydrous diethyl ether. The product is purified by chromatography over silica gel (elution with dichloromethane). The product is a mixture of the cis- and trans-double bond isomers and is used as such, mp 78°–120° C.

EXAMPLE E

Preparation of Hexahydro-5-oxo-1H-pyrrolizine-3-carboxylic acid

A solution of hexahydro-5-oxo-1H-pyrrolizine 3-carboxylic acid ethyl ester (12.6 g, 0.064 mol) in ethanol (35 ml) is treated with a 2N sodium hydroxide solution (35 ml, 0.07 mol) with stirring for 72 hours. The solution is concentrated at reduced pressure and treated with concentrated hydrochloric acid (6 ml) dropwise. The solution is extracted with dichloromethane. The extracts are dried (MgSO4), filtered, and concentrated to yield an oil. Trituration of the oil with acetone yields hexahydro-5-oxo-1H-pyrrolizine 3-carboxylic acid as a white solid with mp 145°–148° C.

I claim:

1. A compound having the structural formula

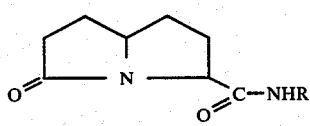

wherein R is $(CH_2)_n NR'R''$ wherein n is one, two, three, or four; R' and R'' are each independently a straight or branched alkyl of from one to six carbon atoms or combined with the nitrogen to form cis- or trans-2,6-dimethyl piperidine which may optionally be substituted with one or more alkyl groups of from one to four carbon atoms; or a pharmaceutically acceptable acid addition salt thereof.

2. A compound according to claim 1 wherein n is two.

3. A compound according to claim 1 wherein n is three.

4. A compound according to claim 1 wherein n is four.

5. A compound according to claim 1 wherein R' and R'' are $CH_3$.

6. A compound according to claim 1 wherein R' and R'' are $C_2H_5$.

7. A compound according to claim 1 wherein R' and R'' $CH(CH_3)_2$.

8. A compound according to claim 1 wherein R' and R'' when taken together with the nitrogen is cis-2,6-dimethylpiperidine.

9. A compound according to claim 1 wherein R' and R'' when taken together with the nitrogen is trans-2,6-dimethylpiperidine.

10. A compound according to claim 1 and being N-[2-[N,N-bis(1-methylethyl)amino]ethyl]-hexahydro-5-oxo-1H-pyrrolizine-3-carboxamide.

11. A compound according to claim 1 and being the cis isomer N-[2-[2,6-dimethyl-1-piperidinyl]ethyl]hexahydro-5-oxo-1H-pyrrolizine-3-carboxamide.

12. A compound according to claim 1 and being the trans-isomer N-[2 [2,6-dimethyl-1-piperidinyl]ethyl]-hexahydro-5-oxo-1H-pyrrolizine-3-carboxamide.

13. A compound according to claim 1 and being N-[N,N-dimethylaminoethyl]-hexahydro-5-oxo-1H-pyrrolizine-3-carboxamide.

14. A compound according to claim 1 and being N-[N,N-diethylaminoethyl]-hexahydro-5-oxo-1H-pyrrolizine-3-carboxamide.

15. A compound according to claim 1 and being N-[3-[N,N-bis(1-methylethyl)amino]propyl]-hexahydro-5-oxo-1H-pyrrolizine-3-carboxamide.

16. A compound according to claim 1 and being the cis isomer of N-[3-[2,6-dimethyl-1-piperidinyl]-propyl]-hexahydro-5-oxo-1H-pyrrolizine-3-carboxamide.

17. A compound according to claim 1 and being the trans isomer of N-[3-[2,6-dimethyl-1-piperidinyl]-propyl]-hexahydro-5-oxo-1H-pyrrolizine-3-carboxamide.

18. A compound according to claim 1 and being N-[3-[N,N-dimethylamino]propyl]-hexahydro-5-oxo-1H-pyrrolizine3-carboxamide.

19. A compound according to claim 1 and being N-[3-[N,N-diethylamino]propyl]-hexahydro-5-oxo-1H-pyrrolizine-3-carboxamide.

20. A cognition activating pharmaceutical composition comprising an effective amount of a compound as defined in claim 1 in combination with a pharmaceutically acceptable carrier.

21. A method of treating senility in mammals which comprises administering to said mammal a pharmaceutical composition in accordance with claim 20 in unit dosage form.

22. A method of reversing amnesia in mammals which comprises administering to said mammals a pharmaceutical composition in accordance with claim 20 in unit dosage form.

* * * * *